United States Patent [19]

Weissman

[11] Patent Number: 4,992,049
[45] Date of Patent: Feb. 12, 1991

[54] METHOD FOR APPLYING A VENEER FACING TO TEETH

[76] Inventor: Bernard Weissman, 225 E. 48th St., New York, N.Y. 10017

[21] Appl. No.: 193,328

[22] Filed: May 12, 1988

[51] Int. Cl.$^5$ .............................................. A61C 5/00
[52] U.S. Cl. .................................. 433/215; 433/166; 433/218
[58] Field of Search ................. 433/75, 165, 166, 215, 433/218, 219, 204, 203.1, 223, 226; 264/16, 19, 20

[56] References Cited

U.S. PATENT DOCUMENTS

| | | | |
|---|---|---|---|
| 712,648 | 11/1902 | Callaway | 433/219 |
| 2,250,058 | 7/1941 | Brooks | 433/166 |
| 2,793,438 | 5/1957 | Ashkin | 433/166 |
| 3,449,832 | 6/1969 | Connan | 433/203.1 |
| 4,473,353 | 9/1984 | Greggs | 433/215 |
| 4,473,354 | 9/1984 | Rigaud | 433/218 |
| 4,526,542 | 7/1985 | Kochis | 433/165 |
| 4,579,530 | 4/1986 | McLaughlin | 433/223 |

Primary Examiner—John J. Wilson
Attorney, Agent, or Firm—Paul J. Sutton; Barry G. Magidoff; Anthony Amaral, Jr.

[57] ABSTRACT

The present invention provides a method for securing a veneer onto a tooth substrate comprising removing enamel in a matrix pattern, to a predetermined depth, from the lingual or buccal surfaces of the tooth, removing the remaining outer enamel layer intermediate the matrix pattern, to the predetermined minimum depth, to provide a first, substantially level excavated enamel surface, further excavating a plurality of compact areas on the first excavated enamel surface to an additional predetermined depth therebelow, but without exposing dentin, to form an indexed enamel surface, taking an impression of such indexed enamel surface, and obtaining from said mold a dental veneer, the dental veneer having a first surface which can mate with such indexed excavated enamel surface, and a second outer surface providing an attractive dentitious appearance; and adhering the indexed veneer surface to the indexed enamel surface, so as to accurately place the veneer on a tooth as an attractive outer labial or buccal surface. Preferably, the indexing grooves are undercut to improve adhesion.

Apparatus is also provided for forming compact indexing excavations within an enamel layer of teeth and for forming undercuts in said excavations.

10 Claims, 5 Drawing Sheets

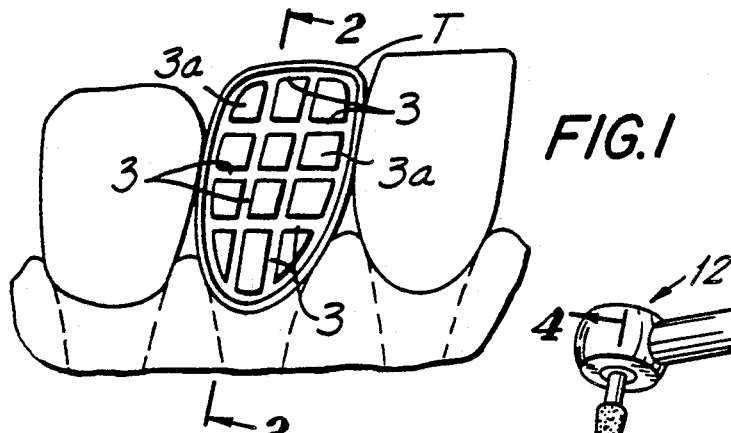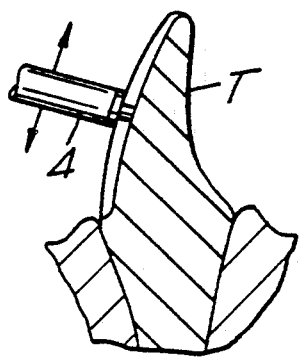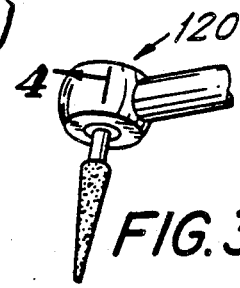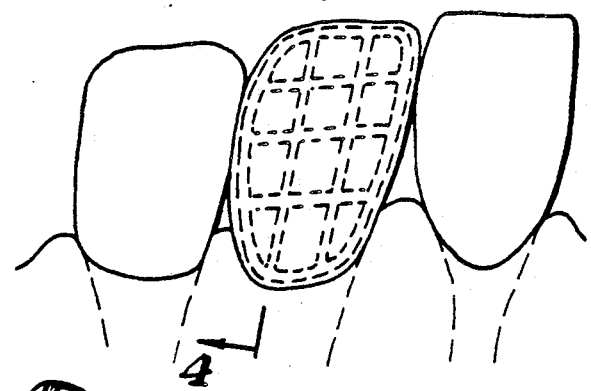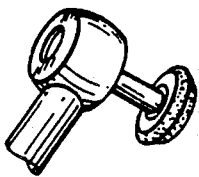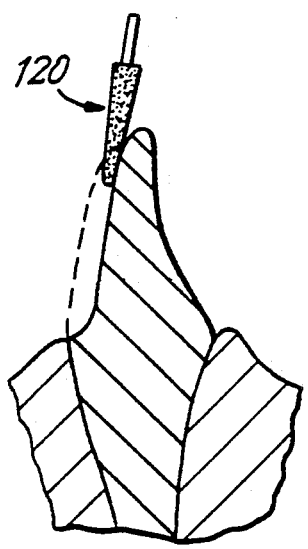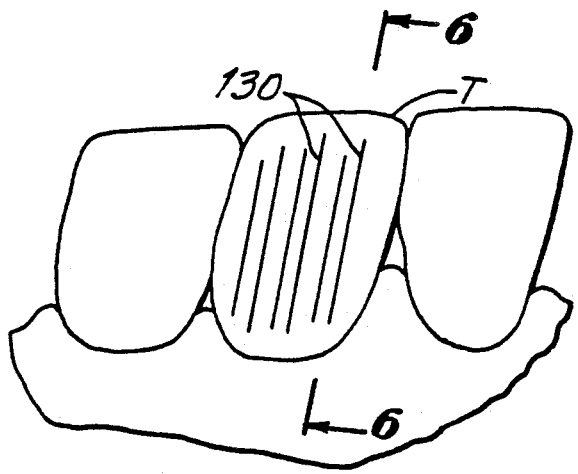

METHOD FOR APPLYING A VENEER FACING TO TEETH

BACKGROUND OF THE INVENTION

The present invention relates to a procedure and to a tool for use in dentistry, and more particularly to an apparatus and a method which provide for the removing of a calibrated amount of dental enamel and for the forming and applying of a veneer facing to a tooth, and particularly with regard to the tool a means for forming a compact indexing excavation for indexing the veneer to be applied.

It is conventional practice in dentistry to apply a veneer facing to a tooth which has been damaged either as a result of trauma or disease, i.e., caries. Generally, the surface enamel of the tooth is partially removed by grinding to form a relatively even surface, a mold is taken of the tooth and the surrounding portions of the mouth to form a facing which is then adhesively secured to the previously ground down surface.

Such a veneer is generally not subject to the extreme structural stress to which the facing transverse surfaces of teeth are subject, but rather it is applied to a vertical buccal or labial surface. Generally primarily for cosmetic purposes as well as to protect the undersurface of the tooth from further damage caused by chemical or bacterial action. Great care must be taken to insure that the veneer is securely applied to the tooth substrate so as to be not only cosmetically satisfactory but also to insure against damage during chewing. The dentist must carefully place the veneer against the surface and by eye insure that it has been properly implaced.

SUMMARY OF THE INVENTION

It is an object of the present invention to provide a procedure and a tool for use in the procedure which improves the efficiency of the process for applying a dental veneer to a tooth while further improving the accuracy with which the veneer is secured and maintained in place. It is a further object of the present invention to provide indexing means to avoid the problems of visually siting and implacing the veneer onto a tooth substrate. It is yet a further object of the present invention to provide tools for more efficiently preparing the tooth for application of the veneer and for securing the veneer to the tooth substrate.

These and other objects are achieved in accordance with the present invention wherein the method of the present invention for securing a veneer onto a tooth substrate comprises removing enamel in a matrix pattern, to a predetermined depth, from the lingual or buccal surfaces of the tooth, removing the remaining outer enamel layer intermediate the matrix pattern, to the predetermined minimum depth to provide a first, substantially level excavated enamel surface, further excavating a plurality of compact areas on the first excavated enamel surface to an additional predetermined depth therebelow, but without exposing dentin, to form an indexed enamel surface, taking an impression of such indexed enamel surface, and obtaining from said mold a dental veneer, the dental veneer having a first surface which is the inverse of the indexed enamel surface on the tooth and which can mate with such indexed excavated enamel surface, and a second outer surface providing an attractive dentitious appearance; and adhering the indexed veneer surface to the indexed enamel surface, using an adhesive, such that the indexed portions on the veneer and on the tooth mate together so as to accurately place the veneer on a tooth as an attractive outer labial or buccal surface. Preferably, the indexing grooves are undercut to improve adhesion.

In accordance with the apparatus of the present invention, a tool for forming compact excavations within an enamel layer of teeth is provided, the apparatus comprising an elongated shank portion, an end of the shank portion designed to be secured to a driving member for causing rotation of the tool, a grinding surface secured to the second end of the shank portion, a depth-limiting surface adjacent to and coaxial with the grinding surface, the two surfaces being aligned in substantially the same direction, and means for accurately varying the perpendicular distance between the depth-limiting surface and the grinding surface. The grinding surface can be planar, substantially perpendicular to the axis of the shank portion or the grinding surface can be circumferential, on the outer surface of a ring, facing in a direction transverse, generally perpendicular to the axis of the shank.

Further details of the present invention are shown in the accompanying drawings, by way of example and not by way of exclusion. Many portions of the invention or the context therefor are shown in schematic representation, where greater detail is unnecessary as it is apparent or well-known to those skilled in the art.

Referring to the accompanying drawings:

FIG. 1 is a front elevation view of a row of teeth, including one with a partially excavated labial surface prepared in accordance with the present invention;

FIG. 2 is a cross-sectional view of a tooth of FIG. 1, taken along lines A—A;

FIG. 3 is a front elevational view of the tooth of FIG. 1 with a fully excavated labial surface of a predetermined depth;

FIG. 4 is a cross-sectional view of the tooth of FIG. 3, taken along lines B—B;

FIG. 5 is a front elevation view of the tooth of Figure, showing an alternative of an indexed excavated surface of the present invention;

FIG. 12 is a perspective view showing one embodiment of a tool in accordance with the present invention;

FIG. 13 is a cross-section view taken perpendicular to the axis of the tool of FIG. 12;

FIG. 14 is a partially exploded, perspective view of another embodiment of a index marking tool of the present invention;

FIG. 15 is an end view of the tool of FIG. 14;

FIG. 16 is a cross-sectional view taken along lines F—F of FIG. 15;

FIG. 17 is a partially exploded perspective view of yet another tool in accordance with the present invention;

FIG. 18 is a cross-section view taken along the axis of the tool of FIG. 17;

FIG. 19 is a side elevation view of an undercutting tool for the present invention;

FIG. 20 is a top plan view of the tool of FIG. 19;

FIG. 21 is an enlarged partial cross-section view of one index mark shown in FIG. 7 being undercut;

FIG. 22 is a enlarged partial cross-sectional view of a mating veneer and indexed tooth surface;

FIG. 23 is an enlarged front view of the tooth index mark of FIG. 22;

FIG. 24 is an enlarged partial cross-sectional view of another embodiment of the veneer of FIG. 23;

FIG. 25 is a partial plan view of the annular ridge shown in FIG. 24; and

FIG. 26 is a cross-sectional view showing the annular groove supporting an orthodontic bracket.

Figure 9:
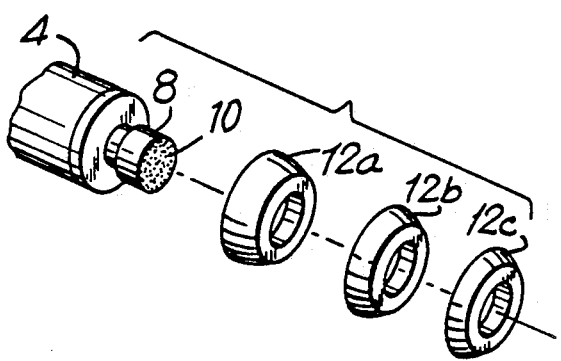
FIG. 9 is a perspective view in partially exploded format, showing a tool for excavating an initial matrix in accordance with the present invention.

Referring to the drawings, an incisor tooth, indicated as "T" in FIGS. 1 and 2 is treated by initially grinding out a matrix of intersecting grooves 3 in the labial surface of the tooth T to a predetermined depth, i.e., half of the thickness of the enamel layer. The grinding of the compact grooves or indentations are carried out, for example, using the grinding tool as shown in FIG. 9, having a rotating transverse grinder surface, and a depth limiting surface. Thereafter, the intermediate material 3a, between the grooves 3, is removed to form a surface 1 of substantially uniform thickness. After the entire surface is ground down to a relatively even condition, so as to remove any damaged or diseased enamel, compact areas in the form of, e.g., straight grooves, or annular grooves, can be formed by further grinding into the excavated surface.

The initial matrix grinder tool (FIG. 9) includes a grinder body 4 having a shank (not shown) designed to fit within any of the commercially available rotary power sources used by dentists, the body 4 is in turn rigidly connected to a neck portion 6 (of reduced diameter) which is in turn connected to a grinder head 8 of somewhat larger diameter. The transversely facing, forward surface 10 of the grinder head 8 has a highly abrasive surface coating, e.g., of fine diamond dust. A stop ring 12 is removably, elastically held in place about the neck portions 6 and between the forward facing annular end surface 104 of the body portion 4 and the rearward facing annular end surface 108 of the grinder head 8. The stop ring is formed of a relatively (compared to enamel) soft, elastic material, such as Teflon, having a low coefficient of friction, so as not to be abrasive to enamel when in contact with the excavated enamel surface of the tooth.

The grinder tool 4 is intended to be rotated by the dentist's rotary drill, such that pressing the rotating grinder surface 10 against the enamel surface of a tooth results in the abrasion and removal of material from the tooth surface.

The grinder tool 4 is used to cut a rough matrix into the tooth enamel to a predetermined depth, determined by the thickness of the stop ring 12. As shown in FIG. 9, stop rings 12 of different sizes, color-coded to indicate thickness, can be individually snapped into place about the neck 6, to achieve the desired depth limit. After the matrix has been cut out, the intermediate unexcavated enamel material 3a can be removed to the same desired depth using, e.g., a conventional cone grinder 120 as shown in FIG. 3. The cone grinder can readily remove the remaining material until a substantially level surface is obtained, at the predetermined depth set by the initial rough matrix cuts.

As an alternative to forming the rough initial matrix on the tooth using the grinder head tool of FIG. 9, the circumferential grinding tool of FIGS. 17 and 18 can be used. This device also provides a abrasive grinding surface 31 formed as an outwardly facing circumferential ring surface about a grinding head, generally indicated by the numeral 27. The grinding head 27 is in turn connected to a drive shaft shank 25, designed to be operatively connected to any of the commercially available rotary dental drills.

The grinding head 27 comprises a central head portion 29 of relatively lesser diameter, the grinding head surface portion 31, of relatively larger diameter, and a relatively lesser diameter inner step surface 28, intermediate the shank 25 and grinding surface 31. Snap-on rings 34, 35 are placed around the inner stop surface 28 and central head surfaces 29, respectively, to act as stops limiting the depth to which a groove can be cut into the enamel tooth surface. By utilizing stop rings 34, 35 of varying thicknesses, varying depths of grooves can be obtained as deemed desirable by the dentist. As the grinding surface 31 is formed of diamond dust, an extremely hard surface, the grinding surface 31 is substantially not at all abraded away during the grinding operation, so as not to affect (reduce) the depth to which the grooves can be cut.

Figure 7:
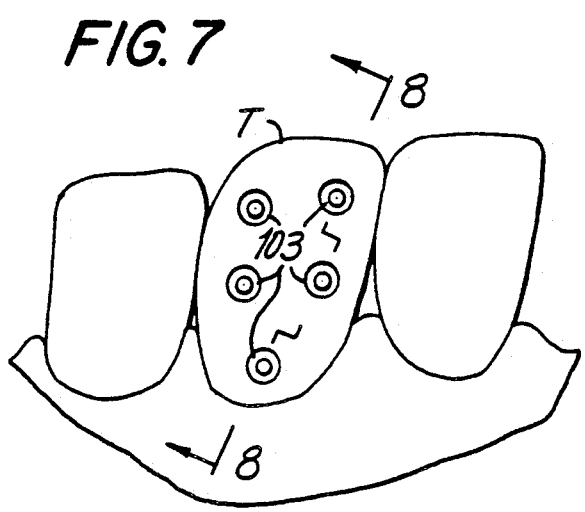
FIG. 7 is a front elevation view of the tooth of FIG. 1, showing a second compact embodiment of an indexed excavated surface of the present invention.

The stop rings 34, 35 can, as shown, be formed in two halves, having snap-in mating prongs and sockets 37, 38, as shown in FIG. 7. Alternatively, the stop rings 34, 35 can be formed as unitary rings, and stretched and snapped into place. To further prevent loosening or accidental loss of the stop rings 34, 35, the mating surfaces of the stop rings 34, 35 and of the head surfaces 29 and 28 are provided with a rib and channel 128, 129 to prevent axial displacement of the rings 34, 35 during high speed rotation. These rings can also be formed of a relatively soft low friction material, such as Teflon.

After the substantially level excavated surface has been obtained, as shown in FIGS. 3 and 4, indexing grooves are formed into the excavated surface. Such grooves can be a variety of shapes and sizes and can include a plurality of non-colinear straight lines or a plurality of substantially circular, preferably annular, grooves.

Figure 6:
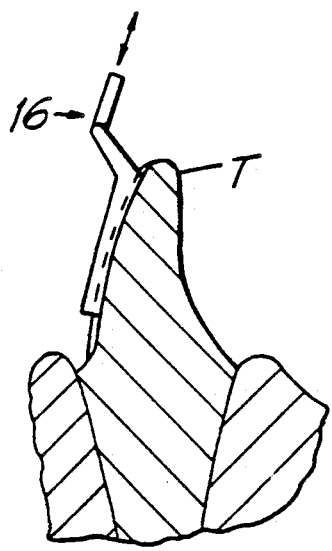
FIG. 6 is a cross-sectional view taken along lines C—C of FIG. 5.

One such series of indexing grooves is shown in FIG. 5 as three parallel linear grooves 130 cut into the excavated surface of the tooth T. As schematically shown in FIG. 6, the three parallel grooves are formed by the linear indexing tool labelled generally by the numeral 16.

The linear indexing tool 16 comprises a drive attachment or shank 18 rigidly secured to a tool body 17 having a generally triangular prismatic shape. The base of the prismatic tool body 17 comprises a ribbed surface, wherein the convex surfaces 22, 20 are abrasive surfaces coated, for example, with fine diamond dust; the two concave intermediate surfaces 24, intermediate the abrasive surfaces 20, 22, provide a stop and are formed of a relatively soft and non-abrasive material, such as Teflon.

Figure 10:
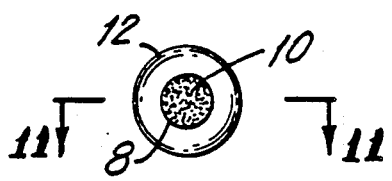
FIG. 10 is an end view of the tool of FIG. 9.
Figure 11:
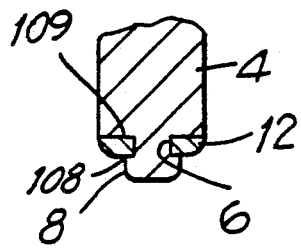
FIG. 11 is a cross-sectioned axial, elevation, view of the tool of FIG. 10, taken along lines E—E.

As shown, the linear indexing tool 16 has axially extending abrading surfaces 20, 22 which are so spaced and have the same width as the rotary grinding tool head 10, as shown in FIGS. 9 and 10. For example, the grinding tool head 10 can have a diameter of about 0.02 inch and the three sets of parallel grooves 3, as shown in FIG. 5, can be separated by approximately 0.02 inch. Accordingly, the refining tool 16 should have three abrasive convex ridge surfaces 20, 22, each ridge having a width of 0.02 inch, separated by non-abrasive concave surfaces 24, each concave surface 24 also having a width of 0.02 inch. Reciprocatingly applying the tool 17 to the excavated surface 1 along a vertical axis results in a precisely formed parallel indexing pattern 130, as shown. The indexing tool 16 can be operated as a hand tool, without mechanical assistance or it can be operated using any of the commercially available reciprocating mechanical dental hand tools, such as the Dentatus reciprocating hand piece, driven by a dentist's rotary drill device.

An alternative indexing pattern comprises the series of annular grooves 103 formed in the excavated tooth surface of FIG. 7. These annular grooves 103 are formed utilizing an annular grinder, as shown in FIGS. 14 through 16. The annular grinder comprises a hollow, tubular tool body, indicated by the numeral 40, One end of the tubular tool body 40 provides an annular grinding surface 44 surrounding a threaded central opening 47. An insert stop 46 having a threaded circumferential outer surface is threadedly secured within the central opening 47, and can be rotated into the opening 47 utilizing a screw driver or the like fitted within the outer slot 48.

Optionally, the inner end of the insert 46 is rigidly secured to a gauge indicator 49, comprising a relatively thin disk rigidly secured to the inner end of the stop insert member 46. A slot opening is formed through the wall of the tubular grinder body 40, adjacent the front grinding head end 44, extending rearwardly, longitudinally parallel to the axis of the tool 40. Gauge index marks 43 are formed along the sides of the window 42, which indicate the depth below the surface 44 of the slot head 48 based upon the location of the gauge indicator 49. Alternatively, inserts 46 of different lengths, as shown in exploded form in FIG. 14, can be screwed to the end of the threads in the central opening 47, thereby providing different predetermined depth limitations, i.e., a shorter insert 46c results in a deeper groove cut into the tooth surface.

Figure 8:
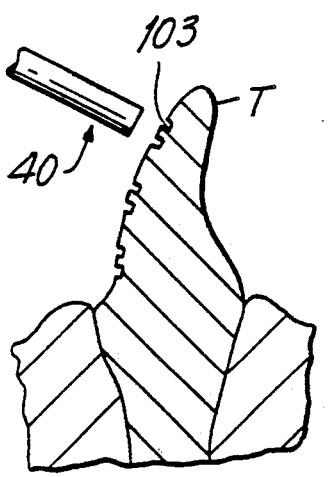
FIG. 8 is a cross-sectional view taken along lines 8—8 of FIG. 7.

The alternative indexing groove formed by the tool of FIG. 14 is shown as annular grooves 103 in FIGS. 7 and 8. The annular groove is cut into the first excavated surface of the tooth as described above for the linear index groove. The annular grinding tool 40 is secured to a conventional rotary dental drill, by a shank portion not shown. By setting the stop insert 46 at a predetermined distance below the surface 44, the depth of the annular groove 103 can be predetermined.

The depth of the annular groove 103 is limited by the central stop gauge member 46 and is predetermined by rotating the member 46, as by utilizing a screw driver in the slot 48, so as to move the member 46 axially toward or away from the grinding surface 44. The distance below the surface 44 of the slotted head surface 48 is indicated by the stop gauge indicator 49 registering with the indicia 43 formed along the outer circumferential surface adjacent to the window 42, or the indicia can be formed on a transparent sheet extending across window 42.

Once the indexed excavated tooth surface is completed, either as the parallel grooves shown in FIG. 5 or by the formation of a plurality of annular grooves, as in FIG. 7, or other multiple compact shapes, an impression is taken of the tooth in accordance with standard dental practice.

By following standard procedures, well known in this art, a veneer is formed wherein one surface of the veneer has formed thereon elements which are mateable with (or complementary to) the indexed excavated surface on the tooth substrate. For example, where the substrate includes the grooved matrix, as shown in FIG. 2, the surface of the veneer will have an inverted convex, or ridged, matrix designed to fit precisely within the groove matrix of the tooth substrate. Alternatively, if a plurality of annular grooves are formed using the annular grinder of FIG. 14, a veneer having the appearance shown in FIGS. 24 and 25 is formed, wherein the annular ridges 61 mate precisely with the complementary, or mateable, annular grooves 103 formed in the tooth substrate.

The indexing grooves formed in the tooth substrate are preferably further treated to provide undercuts 73, preferably towards the innermost portion of the grooves 3, 103. Such an undercut 73 can be formed by a grinding tool, of the type shown, for example, in FIGS. 19 and 20. This grinding tool, generally indicated by the numeral 51, includes a shank 55 shown in part and designed to be secured at its rearmost end to a conventional rotary dental drill. Secured to the forward end of the shank 55 is the undercutting grinding tool head 53. A grinding surface 56 comprises an annular portion 156 on the front transverse face 54 and a second continuous circumferential portion 256 extending around the foremost end of the longitudinal surface of the tool 51. The transverse annual portion 156 and circumferential annual surface 256 meet at the annular grinding apex 56. The central portion of the transverse from end 54 is preferably depressed slightly below the level of the grinding surface 156.

The head of the tool 51 is greatly magnified in these drawings. The outer diameter of the grinding surfaces 156, 256, i.e., the diameter of the circular apex 56, is preferably less than the width of the indexing groove 3,103 formed in the tooth surface, e.g., 0.02 inch.

The head of the undercutting tool 51 is inserted into the indexing grooves 3,103, previously cut into the excavated enamel surface, and the grinding surface apex 56 is pressed against the interior longitudinal surfaces of the grooves preferably against the surface of maximum diameter, so as to form an undercut indentation, such as indentation 73 shown in FIGS. 22 and 23. A further undercut indentation can be formed in the protruding mating surfaces, e.g., 61, on the veneer 2, as indicated by the indentations 65, in FIGS. 22-25. The undercut can be made as a complete annular circle, as in FIGS. 22 and 23, or only partially around the annular ridge, or groove, as exemplified by the undercut ridge 173 of FIGS. 24 and 25.

The veneer 60 can then be accurately applied to the tooth substrate by registering the indexing protrusions 61 with the indexing grooves 3, 103. In this manner, the veneer is accurately aligned on the tooth without requiring the extremely sensitive and exact visual placement necessary with prior art veneers. The indexing members avoid errors which often arise from inaccurate siting of the veneer when applying it to a smooth tooth surface.

Dental veneers of this type are generally secured to the teeth by adhesives, of types generally used in the field. In this case, the adhesive can be applied within the indexing grooves 3 as well as around the indexing convex surfaces 61 with additional material sufficient to fill the undercut grooves 65, 73, in both the convex and concave surfaces. This provides a more positive seal for the veneer to the tooth substrate while also insuring an accurate fit.

The adhesives used for securing the veneer to the tooth substrate are preferably of a type having a relatively low viscosity, to enable flow into the undercut surfaces and to permit the outflow of excess adhesive from within the indexed grooves. Otherwise the materials used for forming the adhesive and constructing the veneer as well as the materials of construction of the tools used in the present invention are well known to those skilled in the art and need not be more fully defined The indexing grooves of this invention, especially the annular type, can also be used for the implacement of orthodontic brackets for braces. The wire brackets can be secured to a shallow annular grooves in each tooth surface, e.g. as shown in FIG. 26. Advantageously, this permits a dentist to make the very shallow marking 150 in the, e.g. labial or buccal, surface of a tooth and then permit a technician to adhere the bracket 152 in place. This also provides an increase in surface area of adhesion, by the depth of the groove.

The patentable embodiments of this invention which are claimed are as follows:

1. A method for securing a veneer onto a single surface of a tooth substrate, the method comprising removing from one of the lingual or buccal surfaces of a tooth the outer enamel layer, to a predetermined minimum depth to provide a first excavated enamel surface; excavating a plurality of compact areas on the first excavated surface to an additional predetermined depth to below the first excavated surface, but without exposing the dentin, to form grooves on an indexed single enamel surface; taking a mold of such indexed enamel surface for the purpose of obtaining from such mold a dental veneer, obtaining a dental veneer having a first indexed veneer surface with convex compact impressions inverse to and mateable with, the indexed enamel surface, and a second outer surface providing an attractive dentitious appearance, and adhering the indexed veneer surface to the indexed enamel surface such that the plurality of compact areas mate with the plurality of compact impressions on the veneer, and the attractive dentitious surface provides an outer labial or buccal surface for the excavated tooth.

2. The method of claim 1 wherein enamel beneath the indexed enamel surface has about 25% to 50% the thickness of the original tooth enamel.

3. The method of claim 2 wherein the indexed enamel surface comprises longitudinal grooves extending below the first excavated surface.

4. The method of claim 3, wherein at least two of the longitudinal grooves intersect at a central portion of the indexed enamel surface.

5. The method of claim 1, wherein the indexed enamel surface comprises a plurality of compact depressions.

6. The method of claim 5, wherein the compact depressions are substantially annular, surrounding a portion of the first excavated enamel surface.

7. The method of claim 6, wherein the compact depressions are generally circular in outline.

8. The method of claim 1, further comprising forming undercut surfaces in the grooves prior to adhering the veneer to the indexed enamel surface.

9. The method of claim 8, wherein the undercut surfaces are formed utilizing a grinding tool comprising a pair of transversely aligned annular surfaces intersecting at a circular apex.

10. The method of claim 1, wherein the first excavated surface is formed by initially grinding out a matrix of grooves in the original tooth surface to the predetermined depth and subsequently removing the remaining surface material adjacent the grooves, to the same predetermined depth.

* * * * *